US005656343A

United States Patent [19]
Baker

[11] Patent Number: 5,656,343
[45] Date of Patent: Aug. 12, 1997

[54] METHOD OF PRODUCING DRIED PLANTS AND OTHER SUBSTRATES AND THE PRODUCT PRODUCED THEREBY

[76] Inventor: Marion A. Baker, 18161 Windsor Dr., Villa Park, Calif. 92667

[21] Appl. No.: 420,063

[22] Filed: Apr. 11, 1995

[51] Int. Cl.⁶ ........................................ A01N 3/00
[52] U.S. Cl. .................. 428/17; 156/57; 427/4; 428/22; 428/24
[58] Field of Search .................. 428/24, 22, 17; 427/4; 156/57

[56] References Cited

U.S. PATENT DOCUMENTS

| 3,645,766 | 2/1972 | Mazzucato et al. | 428/24 X |
|---|---|---|---|
| 4,808,447 | 2/1989 | Baker | 428/24 X |
| 4,885,037 | 12/1989 | Ohkubo | 428/24 X |
| 5,120,583 | 6/1992 | Garcia | 428/24 |
| 5,252,537 | 10/1993 | De Winter-Scailteur | 428/24 X |
| 5,456,776 | 10/1995 | Noguchi | 428/24 X |
| 5,560,965 | 10/1996 | Fukui et al. | 428/24 |

*Primary Examiner*—Henry F. Epstein
*Attorney, Agent, or Firm*—Sixbey, Friedman, Leedom & Ferguson, PC; Jeffrey L. Costellia

[57] ABSTRACT

The process and product obtained thereby of obtaining substantially dried flower blooms and other natural predominantly carbohydrate products such as flower stems, leaves, other vegetable matter and insects, which substantially retain their original shape and color, comprising the steps of covering the substrate with particulate matter and then subjecting the covered substrate to a reduced pressure environment to remove most of the water from the substrate.

18 Claims, No Drawings

METHOD OF PRODUCING DRIED PLANTS AND OTHER SUBSTRATES AND THE PRODUCT PRODUCED THEREBY

BACKGROUND OF THE INVENTION

1. Technical Field of the Invention

The present invention relates to a process of obtaining dried flower blooms and other dried, natural products such as flower stems, leaves, fruits, vegetables and insects. The invention also relates to the product resulting from the process.

2. Description of the Related Art

Drying flowers is one of man's oldest activities. Archaeologists often find dried flowers among the artifacts of ancient peoples. Modem scientific methods of drying probably started with Ernst Pfitzer, a professor who in Heidelberg, Germany invented the process of solvent dehydrating flowers (1895 U.S. Pat. No. 547,227). At an unknown time prior to Professor Pfitzer, drying flowers with warm forced air (kiln drying) was invented (perhaps at the beginning of the machine age). During World War II a high water absorbent capacity silica gel was first made and immediately became widely used for drying flowers. Silica gel drying produces flowers of higher quality and durability than air, but slow drying times and high labor costs limited it's commercial application. Another important development during WW II was the vacuum freeze drying process which was perfected and used primarily for the production of pharmaceuticals. Only during the last 10 years has vacuum freeze drying been used commercially to dry flowers.

Four drying processes are widely used in commerce today: 1) Traditional air drying achieved by hanging flowers in warm, dry places; 2) Hot air kiln drying is used to produce bunches of low quality dried flowers in a short time; 3) Silica gel drying is used by florists, botanical gardens and hobbyists that are interested in high quality, long lasting dried flowers; and 4) Vacuum freeze dried flowers which are a fast growing market segment because attractive flowers can be produced with little labor. Unfortunately, vacuum freeze dried flowers are filled with voids left by the removed ice and water. ("Freeze dried" flowers is a bit of a misnomer since most of the hydrogen oxide is removed from the melted liquid and not by sublimation). The voids make the dried flowers fragile and cause rapid fading of color. The flower sealer described in my U.S. Pat. No. 4,783,351 is useful in minimizing, but not completely remedying, these shortcomings. Other deficiencies of vacuum freeze drying are the long process times of 7 to 14 days, the high cost of the equipment and reported frequent, costly equipment failures.

My present invention combines the better features of silica gel drying with the better features of vacuum freeze drying in that the dried flowers are produced quickly and with comparatively simple equipment. The dried flowers are compressed by the force of the vacuum on the silica gel and are also free of voids caused by freeze drying. Their colors are brighter and longer lasting than those made by any other known process.

Many attempts have been made in the past to speed-up the silica gel process for drying flowers by heating the covered flowers. All have been relatively unsuccessful because the heat needed to substantially increase drying time at ambient pressure significantly degrades flower colors. Also, the high heat softens the flower to such an extent, before it has lost all it's moisture, that the sharp silica gel becomes imbedded in the flower. When the flower is completely dried the silica gel cannot be removed.

SUMMARY OF THE INVENTION

The present invention comprises the process of obtaining dried flower blooms and other dried, natural products such as flower stems, leaves, fruits, vegetables and insects (hereafter "substrate") by covering the fresh material with particulate matter and placing the covered objects in a reduced pressure vessel for a period of time necessary to remove most of the water that was present in the material before it was covered.

This invention also includes the product prepared by covering the substrate with particulate matter and placing it in a reduced pressure vessel for a period of time necessary to remove most of the water from the substrate.

This invention also includes a method of treating particulate matter with hydrophobic materials in order to facilitate removal of the particulate matter from the dried substrate.

This invention also includes a new method of vibrating the particulate matter while it is covering the substrate, thus "fluidizing" the particulate matter to achieve more uniform and dense packing around the parts of the substrate, thus increasing dehydrating efficiency, without deforming the covered parts.

It is an object of this invention to provide a new method of drying flowers and other predominantly carbohydrate substrates.

It is a further object of this invention to provide a rapid and economical method of drying flowers, other predominantly carbohydrate matter and selected matter of animal origin.

It is yet another object of this invention to provide more aesthetically pleasing preserved flowers, other predominantly carbohydrate matter and matter of animal origin.

These and other objects and advantages of this invention will be apparent from the more detailed description which follows.

DESCRIPTION OF THE PREFERRED EMBODIMENTS

PARTICULATE MATTER CHOICES, THEIR CHEMICAL TREATMENT AND APPLICATION VIA VIBRATION

Silica gel, in my experiments to date, is the preferred particulate matter for surrounding a specimen to be dried. However, many other choices are available that provide suitable results.

The required characteristics of a suitable particulate matter include:

1) A particle size that is preferably between 20 and 200 screen mesh size. However, small amounts of particles below and above these sizes can be tolerated.

2) The particles should not be softened or dissolved by small amounts of water liquid or vapor that typically exists the substrate during drying. A material that softens or dissolves will almost always become "glued" to the dried substrate. However, if the surface of the particles are pre-treated with a water repellant material, slight softening of the particles will not noticeably affect the appearance or durability of the dried substrate since the softened particles can be easily removed from the substantially dried substrate.

3) The apparent particle density must be sufficiently high so as to hold flower petals "in place" as they dry, yet not be so extremely dense as to deform the flower petals. Particles with an apparent density of about 0.5 to about 2.0 are preferred. A material such as the filter aid made from diatoms (diatomaceous earth) is not dense enough to function properly when used alone. Coated iron particles such as iron filing are too dense to function properly when used alone.

4) The particles should be non-volatile under the conditions of use (Except for absorbed or hydrated water content).

5) Particles with high surface areas are preferred. The speed at which the substrate loses water is, in part, dependent on the ability of the particles to "wick" water away from the substrate. The wicking action is, in turn, partly dependent upon the surface area of the particles.

6) Particles with "sharp" edges are often preferred to those with rounded edges. Some of the substrate's cells are cut by the "sharp" edged particles as they are vibrated against the substrate. This cutting action hastens the exist of moisture from the substrate. However, when delicate flowers such as Japanese Iris are dried, sharp particles can become permanently "glued" to the petals due to the penetration of the particles into the fresh, tender surfaces. higher temperature exacerbate this problem.

7) Particle pH is sometimes important. Silica gel is slightly acidic and is presumed to actually donate protons to the substrate during drying, thus brightening many colors. Freshly broken glass is also a proton donor. Neutral materials such as ordinary washed sand or corn starch seem to fade but not otherwise change flower color. The color is increasingly faded as the temperature is increased. Strongly basic materials such as calcium oxide and calcium hydroxide usually change the color to purple, lavender, blue or black. However, if the bloom is protected by an impervious layer, this effect may be reduced.

8) Particles that absorb or hydrate water usually dry flowers faster and often yield better quality than do other types of particles. A few examples are silica gels, aluminum silicates, aluminum chlorohydrate, the partial hydrates of the alkali salt of the oxyacids or boron and calcium sulfate anhydrides and partial hydrates.

9) Particles that chemically react with water (as distinguished from being hydrated by water) are also useful as described in 7) above. Examples are calcium oxide, barium oxide and aluminum isopropoxide.

Ordinary clean river or beach sand can be used although extended drying times are required. The more sharp edges the sand has, the faster it works. Sand with many "sharp" edges works better than sand that is "rounded".

A material known as silica gel/almumina hydrogel, when dried, is another alternative. This product is relatively expensive but it's acid nature enhances the color brightness and durability of pink and red flowers.

Natural and synthetic zeolites (also known as molecular sieves) function well as particulate covering for flowers if they are crushed to the appropriate size. They have a larger water capacity than does silica gel or other absorbents, but are expensive and require high temperature regeneration in a separate oven.

Another attractive alternative to silica gel is acid clay desiccants that are commercially available from many sources. These materials are low in cost and easy to regenerate but have, heretofore, not been considered to be a useful alternative because they are slightly water soluble. However, if they are treated with suitable water repellents (such as fluorocarbons, hydrocarbon, silicon containing compounds or mixtures thereof) they become an acceptable for use in drying.

Other alternatives include crystalline salts, cornmeal and particles made from dense woods.

CHEMICAL PRETREATMENT OF THE PARTICULATE MATTER

The use of fluorocarbons, fluorocarbon/hydrocarbon/silicone containing mixtures or oils, waxes and polymers containing hydrocarbons as parting aids when applied to silica gel or other particulate covering materials is new to the flower drying industry.

It was unexpected to find, for example, that silica gel treated with a fluorocarbon containing material such as 3M's Scotchguard[1] Fabric Protector or duPont's Zonyl brand of industrial fluorocarbons or olive oil will achieve easy parting of silica gel from flowers and tighter packing of silica gel around the flowers without noticeably affecting the performance of silica gel as a drying facilitator in this vacuum aided drying process.

[1] Minnesota Minning and manufacturing Co. Trademark.

My early work had shown that vegetable oils such as olive oil, mineral oils such as while oils or compressor oils and a variety of vegetable and mineral waxes function in a similar way as fluorocarbons, but they were not as satisfactory. It is now shown that a combination of a fluorocarbon type substance with these hydrocarbon type substances perform better than either type of substance alone.

Application of the fluorocarbons, silicon containing compounds and/or hydrocarbons to the particulate matter is simple. They are dissolved in a suitable solvent and sprayed on the particulate matter while thoroughly mixing the components. The solvent is evaporated by heating in open air, unless the solvent is water. The treated particulate matter is then placed in a 200–250 degree F. oven for several hours to drive of sorbed solvent or water. The treated particulate matter is then cooled in a closed metal container. It is then ready to use.

VIBRATING PARTICLES AS A TECHNIQUE FOR COVERING SPECIMENS

A container (such as a rounded, plastic cereal bowl) holding substrate is vibrated using mechanical or sonic vibrations. The particle matter that is to be used to cover or imbed the substrate is applied around the flower while the container is vibrating. The particle matter flows, much like a fluid, around the substrate filling all the air spaces that are large enough to allow particle entry. This procedure "packs" the silica gel evenly around the substrate thus supporting the substrate without deforming it. Also the "packing" effect provides more particulate matter at the substrate/particle interface and near the substrate/particle interface thus allowing more efficient drying of the substrate than would otherwise be achieved.

Alternatively, the container can be vibrated intermittently after succeeding portions of particle matter are poured around and, finally, on the substrate.

In it's simplest form, the process consists of surrounding the substrate, which may, for example consist of a freshly opened rose bloom in low water content silica gel particle matter and placing the composite in a low pressure vessel equipped with an operating vacuum pump for such time as is necessary to remove most of the water in the substrate.

Many successful variations on this simple scheme are possible. However, all share the five commonalities of: Water containing substrates that are covered with particulate matter, subjected to pressures below one atmosphere and temperatures below 180 degrees F. for a time necessary to remove most of the water.

The six major process variables are:
1. The substrate utilized.
2. The particle matter utilized.
3. The methods used to cover the substrate with particles.
4. The temperature at which the process is operated.
5. The pressure at which the process is operated.
6. The length of time the process is operated.

EXAMPLE 1

A "Bridal Pink" rose bloom (¾ open) was cut to a stem length of 1 inch below the toms. The 1" stem and toms was scraped on one side by sliding the side of a ¼" electric drill bit along the length to remove a swath of the waxy cutin layer. The bloom was then placed in a polyethylene plastic cup measuring 4" in diameter and 3" in depth. Finely crushed silica gel was poured around the substrate, into the bowl, while vibrating the bowl on an FMC vibrator (used for aligning paper edges) until the bloom was completely covered, taking care to pour the around but not directly on the flower. This procedure allowed the to flow around the petals and into all the small apertures of the bloom by utilizing a technique known as "fluidized bed", in which the behaves as if it were a liquid: The composite of bloom, and bowl were then placed in a vacuum chamber maintained at a pressure of 70 mm of mercury (a gauge reading of 690 mm of mercury). The chamber was then brought to and held for 8 hours at a temperature of 130 degrees F. as measured on the metallic skin of the glass wool insulated container. The temperature of the silica gel in the bowl was measured to be 125, degrees F. upon it's removal from the chamber.

The silica gel was immediately and carefully poured away from the dried rose bloom leaving it intact and dry. The shape appeared to be unaltered by the process, the pink color was a bit more intense and bright than that of the fresh bloom. The petals were sturdy and on close examination appeared to be somewhat compressed. Subsequent ageing studies have shown the colors to be quite durable and much longer lasting than the colors in freeze dried roses. The shape was also more resistant to change than the shape of freeze dried roses under high humidity conditions.

EXAMPLE 2

A "Sonia" rose bloom on a 1" stem was prepared in the same manner as described in Example 1. However, it was dried at a temperature of 100 degrees F. and a pressure of 70 mm of mercury for 24 hours. Upon removal, it was rather dry, but still contained more water than is needed to be stable. However, it's color was found to have changed to an attractive bright pink and it's shape was unaltered. The bloom was immediately placed in a sealed container, along with very dry silica gel, for five days at 60–70 degrees F. temperature. At the end of this time the bloom was completely dry and exhibited the same properties as the bloom in Example 1.

EXAMPLE 3

A fresh lemon was cut in half and one half was separated from the peel, leaving the pith in place. The pithy part of the peel was moist. When silica gel was rubbed over the pith, it became covered with the silica gel. The outside of the peel was free of silica gel. The silica gel peel was placed in a vacuum chamber at a pressure of 70 mm of mercury and a skin temperature of 135 degrees F. for a period of 24 hours. It was dry upon removal and had lost virtually no color or shape. The silica gel that still adhered to the dried pith was easily removed by rubbing with my thumb.

EXAMPLE 4

A recently dead monarch butterfly was covered, as in Example 1 and placed in a vacuum chamber held at 70 mm of mercury and a skin temperature of 120 degrees F. for a period of 24 hours. When removed, the butterfly was completely dry. There was no discernable change in size shape or color.

EXAMPLE 5

A "Sonia" rose bloom on a 1" stem was prepared in a manner as described in Example 1. It was then placed in a vacuum chamber and held at a pressure of approximately 20–50 microns of mercury and a temperature of 68–72 degrees F. for 14 hours. At the end of that time the silica gel was removed and the bloom was found to be dry without discernable change in shape. As in Example 2, the color had turned to a bright pink.

EXAMPLE 6

A "Sonia" rose bloom on a 1" stem was prepared in a manner as described in Example 1. It was then placed in a vacuum chamber and held at a pressure of approximately 20–50 microns of mercury and an initial temperature of minus 18 degrees F., increasing gradually to 32 F. degrees over a period of 8 days. The temperature was raised to 70 degrees F. and held for 24 hours. The vacuum was then released and the container removed and emptied.

The flower bloom had turned to a bright pink with no discernable change in shape. The bloom appeared to be less porous than a conventionally processed "vacuum freeze dried" rose.

EXAMPLE 7

Fresh daffodil, pansy, periwinkle, geranium and St. Anne's lace blooms as well as leaves from a "Sonia" rose were each placed in separate containers and processed in the same way and under identical conditions to those used in Example 1 except none were scraped with an electric drill. All of these blooms were uncovered after 8 hours and found to be dry with no discernable change in shape or color of the blooms. The leaves lost no shape but were not as bright and shiny as they were when fresh.

EXAMPLE 8

Fresh Cymbidium orchid, azalea, Japanese iris, pink tulip and red tulip blooms were placed in separate containers and covered with silica gel while vibrating the containers. The containers with blooms were then placed in a vacuum container held at 70 mm of mercury and 125 degrees F. for 8 hours. None of the blooms were dry at the end of 8 hours nor had they lost enough water to hold their shape when not supported by silica gel. The experiment was repeated, utilizing the same flower blooms, all of which were prepared and treated in the same way except they were maintained at 70 mm of mercury and 125 degrees F. for 24 hours. After the 24 hours all of the blooms held their shape when displayed as free standing blooms in air, but none were dry enough to maintain their shape for a period of several hours in high relative humidity air. All of the blooms were then placed in a sealed container that also held a quantity of the chemical drying agent calcium sulfate anhydride. After one week in this environment all were completely dry. The pink and red colors had darkened but there were no discernable change in shape. The Japanese Iris did not change color at all but the underside of it's petals and sepals were covered with a thin crust of strongly adhering silica gel particles.

EXAMPLE 9

Two pounds of a particulate clay called "DESI PAK D", made by United Desiccants Co. in Belen, N. Mex. was pre-treated by spraying a 2% solution in acetone of Du Pont Chemical Company's product; "ZONYL TBC fluorotelemer intermediate" on the clay while thoroughly mixing. The acetone was then evaporated from the clay by spreading it to a depth of about 1" on metal pans and heating in open air with infra-red lamps. The treated clay was then placed in an oven and held at 250 degrees F. for 4 hours to rid the treated clay of sorbed water.

A "Sonia" rose bloom with 1" stem was then placed in a small polystyrene bowl and covered with the treated clay described above. The bowl was then placed in a vacuum chamber. The pressure was lowered to 70 mm of mercury and the temperature raised to 125 degrees F. and held for 18 hours. When the clay was removed, the rose was dry enough to maintain it's shape while standing free. It's color was about the same as the rose in Example 1. However, small indentations were seen in the petal leaves, caused by the large particle size of the clay.

EXAMPLE 10

A "Bridal Pink" rose bloom with 1" stem was covered with granulated sodium chloride salt that had been pre-treated with "ZONYL TBC"solution as described in EXAMPLE 8 and placed in a vacuum container at a pressure of 100 mm of mercury for a period of 20 hours at a temperature of 125 degrees F. When the flower was removed form the salt, it was limp and useless. The salt that had been touching the bloom was partly dissolved in water.

EXAMPLE 11

A large lavender red florabunda rose was covered with "ZONYL TBC" treated silica gel and held at a pressure of 70 mm of mercury and a temperature of 125 degrees F. for 9 hours When the rose was removed from the silica gel, it was dry, possessed excellent color and shape and was virtually free of silica gel particles and dust.

EXAMPLE 12

A bright red multiflora rose bloom was covered with the sodium salt of an oxyacid of boron by carefully pouring the particle around the bloom, into a container while vibrating the container and it's contents until the bloom is completely covered. The container and contents was then held at a pressure of 60 mm of mercury and temperature of 125 degrees F. for 8.5 hours.

When the bloom was removed from the container and separated from the particles of salt, it was found to be very near to the fresh bloom with regard to shape and color. There was little residual salt clinging to the bloom.

EXAMPLE 13

The procedure of Example 11 was repeated except white cornmeal treated with "ZONYL FSA Flourosurfactant"[2] made by duPont Chemical Co. was used as the particulate flower bloom covering matter.

[2] Trademark of E. T. duPoint Company

When the bloom was removed form the container and separated from the treated corn meal, it was found to be unchanged in shape but the red color somewhat faded. There was little residual treated corn meal clinging to the bloom.

EXAMPLE 14

Thinly sliced pieces of lean beef and pork were covered with cornmeal that had been previously oven dried for six hours at a temperature of 200 degrees F. and ambient pressure. The covered meat was placed in a vacuum chamber and held at a temperature of 130 degrees F. and a pressure of 125 millimeters of mercury for a period of 18 hours. Slices of uncovered beef and pork were also placed in the vacuum container for comparison purposes. When the corn meal meat was removed, it was found to be virtually dry and had noticeably shrunk "withered". The dried meat tasted much like fresh, uncooked meat although it was "chewy" in the manner of "Jerky". The uncovered slices of meat had also dried substantially, but were noticeably not as dry as the covered meat slices and had not noticeably shrunk. The corn meal appears to have quickened the drying process.

Having fully described the invention, it is intended that it be limited only by the lawful scope of the appended claims.

I claim:

1. A process of obtaining substantially dried flower blooms, flower stems, leaves and other vegetable matter, which substantially retain their original shape and color, comprising the steps of covering the surface area of a substrate to be dried with particulate matter, wherein the substrate is at least one of a flower bloom, a flower stem, leaves, or other vegetable matter which contains water therein, and then subjecting the substrate covered with the particulate matter to a reduced pressure environment to remove substantially all of the water from the substrate, wherein the particulate matter in intimate contact with the surface area of the substrate acts as an exchange agent facilitating the removal of the water from the substrate.

2. The substrate is at least one of a flower bloom, flower stem, leaves, or other vegetable matter having substantially all of said water removed therefrom produced by the process of claim 1.

3. The process of claim 1 wherein the pressure of the reduced pressure environment is between the range of 10 microns to 600 millimeters of mercury.

4. The process of claim 1 wherein the substrate, when in the reduced pressure environment, is subjected to heat.

5. The substrate produced by the process of claim 4.

6. The process of claim 4 wherein the substrate, when in the reduced pressure environment, is subjected to heat within the range of between 65 degrees Fahrenheit to 180 degrees Fahrenheit.

7. The process of claim 4 further comprising the step of vibrating the particulate matter and substrate in such a manner as to cause the particulate matter to flow and thus encase the surface area of the substrate.

8. The process of claims 1, 4, or 7 wherein the particulate matter has been selected from the group consisting of silica gel, river sand, hydrated hydrogels, synthetic and natural zeolites, alumina, clays, crystalline inorganic salts, aluminum chlorohydrates, calcium oxide, boron oxide and aluminum isopropoxide.

9. The process as in claims 1,4 or 7 wherein the particulate matter is hydrophobic.

10. The process as in claims 1, 4, or 7 wherein the particulate matter has been treated with a fluorocarbon containing compound.

11. The substrate is at least one of a flower bloom, flower stem, leaves, or other vegetable matter having substantially all of said water removed therefrom produced by the process of claim 8.

12. The substrate is at least one of a flower bloom, flower stem, leaves, or other vegetable matter having substantially all of said water removed therefrom produced by the process of claim 9.

13. The substrate is at least one of a flower bloom, flower stem, leaves, or other vegetable matter having substantially all of said water removed therefrom produced by the process of claim 10.

14. The process according to claims 1 or 4 wherein when the substrate is a flower bloom, said flower bloom including a flower torus, pedicel, stem and cutin layer, the process further comprising first scraping at least one of the flower toms, pedicel and stem to remove on at least one side the cutin layer before it is enclosed within the particulate matter.

15. The substrate is at least one of a flower bloom, flower stem, leaves, or other vegetable matter having substantially all of said water removed therefrom produced by the process of claim 14.

16. A process of obtaining substantially dried flower blooms, flower stems, leaves, and other vegetable matter, which substantially retain their original shape and color, comprising the steps of covering the surface area of a substrate to be dried with silica gel, wherein the substrate is at least one of a flower bloom, a flower stem, leaves, or other vegetable matter which contains water therein, and then subjecting the substrate covered with the silica gel to a reduced pressure within the range of between 10 microns and 600 millimeters of mercury and heat between 65 degrees Fahrenheit to 180 degrees Fahrenheit to remove substantially all of the water from the substrate.

17. The substrate is at least one of a flower bloom, flower stem, leaves, or other vegetable matter having substantially all of said water removed therefrom produced by the process of claim 16.

18. A process of obtaining substantially dried flower blooms, flower stems, leaves and other vegetable matter, which substantially retain their original shape and color, comprising the steps of: covering the surface area of a substrate to be dried with particulate matter, wherein the substrate is at least one of a flower bloom, a flower stem, leaves, or other vegetable matter which contains water therein, and wherein the particulate matter in intimate contact with the surface area of the substrate acts as an exchange agent facilitating the removal of substantially all of the water from the substrate;

vibrating the particulate matter and substrate in such a manner as to cause the particulate matter to flow and thus encase the surface area of the substrate.

\* \* \* \* \*